(12) United States Patent
Beattie

(10) Patent No.: US 7,445,338 B1
(45) Date of Patent: Nov. 4, 2008

(54) SLIT LAMP TABLE

(76) Inventor: Brian Beattie, 3218 Crocus Ave., Bismarck, ND (US) 58501

( * ) Notice: Subject to any disclaimer, the term of this patent is extended or adjusted under 35 U.S.C. 154(b) by 0 days.

(21) Appl. No.: 11/581,977

(22) Filed: Oct. 17, 2006

(51) Int. Cl.
*A61B 3/10* (2006.01)
(52) U.S. Cl. .................................. 351/214; 351/245
(58) Field of Classification Search ............. 351/200, 351/214, 245
See application file for complete search history.

(56) References Cited

U.S. PATENT DOCUMENTS

| | | | |
|---|---|---|---|
| 4,022,136 A | 5/1977 | Schott | |
| 4,187,005 A * | 2/1980 | Rosenberger | 351/245 |
| 4,796,859 A | 1/1989 | Ventura | |
| 6,631,990 B2 | 10/2003 | Schippert et al. | |
| 6,712,470 B2 * | 3/2004 | O'Brien et al. | 351/245 |
| 6,739,653 B1 | 5/2004 | Hoekstra | |
| 2007/0171372 A1 * | 7/2007 | Seal et al. | 351/245 |

* cited by examiner

*Primary Examiner*—Huy K Mai

(57) ABSTRACT

A new and improved slit lamp microscope table with a front recess of suitable size to accommodate the torso of the occupant of a wheel chair or an obese individual. With the table set at an appropriate elevation, the handicapped individual can move his or her wheel chair to the vicinity of the table. The wheel chair is rolled toward the table until the user is located with his or her torso in the recess. Once the patient is in position, the table can be lowered to the point at which the arm rests of the table come into contact with the arms on the wheel chair and more positively hold the table and wheel chair in the desired relation.

5 Claims, 2 Drawing Sheets

SLIT LAMP TABLE

FIELD OF THE INVENTION

This invention relates to a table for the placement of a slit lamp microscope, laser or similar instrument and more particularly to a table for a slit lamp microscope, laser or similar instrument with the front surface being concave to receive the torso of a person seated at the table having his or her eyes examined or treated.

BACKGROUND OF THE INVENTION

A variety of tables for supporting a slit lamp microscope and other eye examination and treatment instruments have been developed over the years and are known in the art. In the prior art, a slit lamp assembly generally included a base with a generally vertical upstanding standard and a table. Conventionally, the upstanding standard includes means to adjust the table height, which may be pneumatic or, in a simple form, a pair of telescoping tubes with a pin to maintain an adjusted height. In any event, means are provided to adjust the table to accommodate the particular individual whose eyes are being examined.

The examination takes place by use of a device known as a slit lamp microscope. The slit lamp microscope sits upon the top side of the table. When being examined, the patient must place his or her chin on a chin support contained on the slit lamp microscope and must rest his or her forehead on a forehead support contained on the slit lamp microscope. The proper placement of a patient's chin and forehead is essential to ensure the patient's head remains in a fixed position when using the slit lamp microscope to examine or treat the patient's eyes.

The prior art slit lamp table has a top side and a bottom side, two lateral end edges and two longitudinal side edges. The prior art slit lamp table is in a rectangular shape. The prior art tables for a slit lamp microscope do not contain any centrally located recess or opening on the front end edge of the table so as to allow a person's torso to be closer to the slit lamp microscope during examination or treatment.

Accordingly, it is the primary object of the present invention to provide a table for a slit lamp microscope, laser or similar instrument with a centrally located recess or opening at the front end edge of the table to receive the torso of a patient seated at the table.

It is the further object of the present invention to provide a slit lamp table with a centrally located recess or opening and chin and forehead supports located above the centrally located opening and supported by means so as to not impede the opening.

It is the further object of the present invention to provide a slit lamp table with a recess or opening which is relatively inexpensive and easy to manufacture and more patient friendly as compared with the prior art.

Other objects and advantages of the present invention will become obvious to the reader and it is intended that these objects and advantages are within the scope of the present invention.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

SUMMARY OF THE INVENTION

The present invention provides a new and improved table for a slit lamp microscope having a centrally located recess or opening at the front end edge to receive the torso of the patient having his or her eyes examined. The present invention further provides a means for locating the chin and forehead supports above the opening. The fixture containing the chin and head supports is supported through a pair of angled brackets attached to the sides of the table so as not to interfere with the centrally located opening.

The prior art slit lamp table is not conducive, and causes difficulties, when using a slit lamp microscope to examine the eyes of an individual in a wheel chair or an overweight individual. Many individuals who are confined to wheel chairs temporarily or for extended periods of time have need for eye examinations using a slit lamp microscope. For such people the prior art slit lamp table is quite unsuitable because the rectangular nature of the prior art slit lamp table makes it difficult for an individual confined to a wheel chair to get close enough to the slit lamp microscope to properly rest his or her chin on the chin support and his or her forehead on the forehead support. The inability of the wheel chair confined individual to properly rest his or her chin and forehead on the supports could result in inaccurate testing results or the inability to test the individual's eyes.

Likewise, an overweight or obese person is limited in his or her ability to get close enough to the slit lamp microscope to properly place his or her chin and forehead in the chin and forehead supports due to the rectangular nature of the prior art tables holding the slit lamp microscope.

The present invention allows an individual confined to a wheel chair or an obese individual to move his or her torso closer to the slit lamp microscope thereby placing the individuals head closer to the slit lamp microscope resulting in the proper placement of the patients chin and forehead on the chin and forehead supports to ensure accurate testing or treatment results.

The front end of the table is provided with a centrally located recess of suitable size to accommodate the torso of the occupant of a wheel chair or an obese individual. With the table set at an appropriate elevation, the handicapped individual can move his or her wheel chair to the vicinity of the table. The wheel chair is rolled toward the table until the user is located with his or her torso in the recess. Once the patient is in position, the table can be lowered to the point at which the arm rests of the table are situated between the arm rests of the standard wheel chair.

The width of the table is adequate for the examination of the patient's eyes with the slit lamp microscope without excessive side overhang and its length is great enough to allow an individual confined in a wheel chair to move into position in the recess. The total length of the prior art stand will only be a minor portion of the length of the table so that there are no floor obstructions beneath the outer portion of the table to impede the placement of a wheel chair. It has been determined that suitable dimensions for the table are a width in the range of 15 to 22 inches, a length in the range of 14 to 24 inches, and a recess opening in the range of 12 to 15 inches wide and 3 inches deep.

There has thus been outlined, rather broadly, the more important features of the present invention in order that the detailed description thereof may be better understood, and in order that the present contribution to the art may be better appreciated. There are additional features of the invention that will be described hereinafter and that will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

DETAILED DESCRIPTION OF THE PREFERRED EMBODIMENTS

Before explaining the disclosed embodiment of the present invention in detail it is to be understood that the invention is not limited in its application since the invention is capable of other embodiments. Also, the terminology used herein is for the purpose of description and not of limitation.

Figure 1:
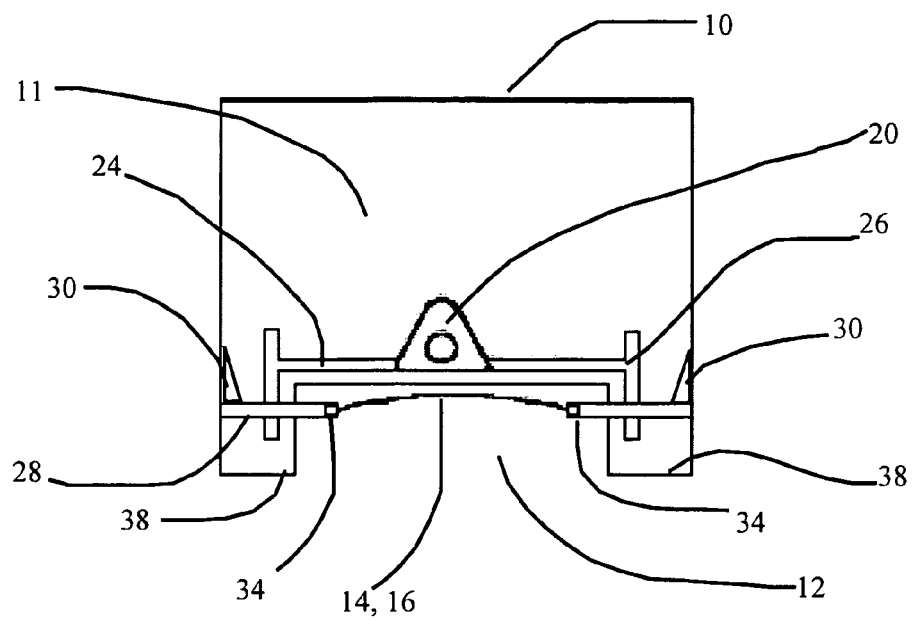
FIG. 1 is a top perspective view of the principal embodiment of the present invention.
Figure 2:
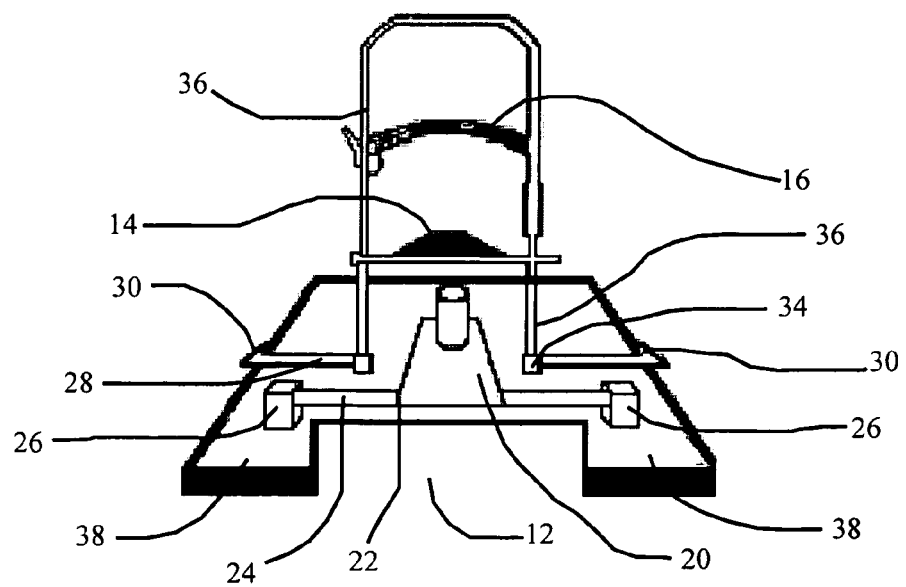
FIG. 2 is a front perspective view of the principal embodiment of the present invention with a slit lamp microscope.
Figure 3:
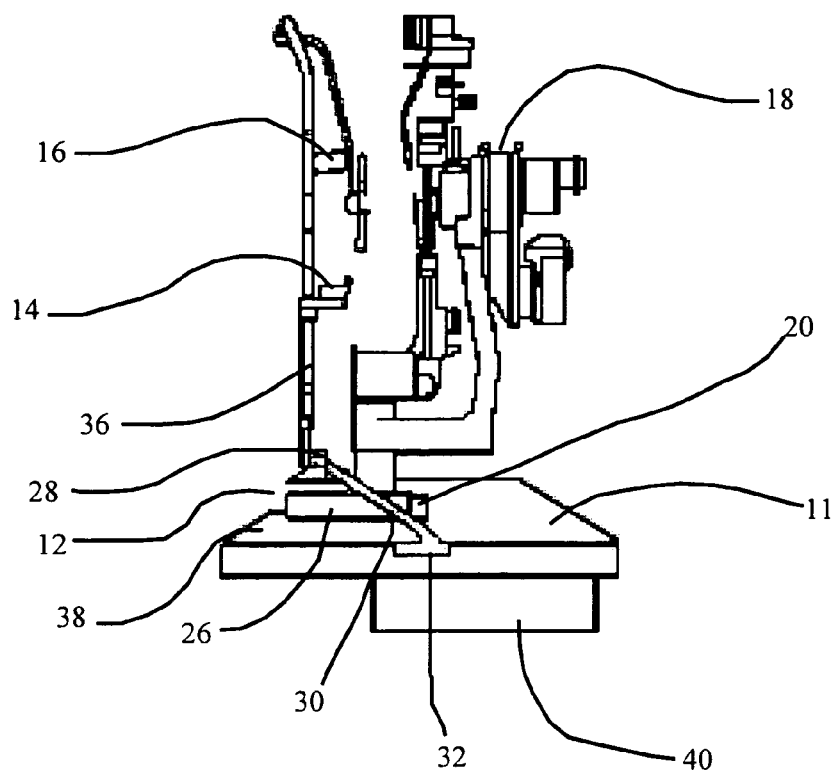
FIG. 3 is a side perspective view of the principal embodiment of the present invention.

The apparatus of the invention is schematically illustrated in FIGS. 1, 2 and 3, in which a slit lamp table 10 is illustrated having a centrally located front recess 12, a chin support 14, a forehead support 16 and a movable slit lamp microscope 18. A variety of means can be utilized to support and adjust the table to accommodate the particular person whose eyes are being examined or treated. The preferred method for supporting the table would include a support base located to the side of the table with a pivoting arm (not shown) attached to the bottom side of the table.

The slit lamp table 10 is a generally planar narrow elongated panel 11 having a top side, a bottom side, two longitudinal side edges, a front lateral end edge, and a back lateral end edge. The front lateral end edge of the elongated panel 11 is formed with a front recess 12 of sufficient width and depth to accommodate the torso of a wheel chair occupant or overweight individual who is having his or her eyes examined or treated with the slit lamp microscope 18.

The front recess 12 cooperates with the side margins of the elongated panel 11 to define a pair of outward extensions 38. The patient to be examined or treated is positioned in front of and within the front recess 12. When the patient is properly positioned about the front recess 12, the outward extensions 38 are astride the patients sides so as to act as arm rests or can be placed upon the arms of a wheel chair to provide further support for the elongated panel 11 during the treatment or examination.

The examination takes place by use of a device known as a slit lamp microscope 18. The slit lamp microscope 18 is supported and maintained on the elongated panel 11 by means of a triangular shaped slit lamp base 20. The slit lamp base 20 has a first end, a second end, a first side and a second side. The slit lamp base 20 is movably attached to the top side of the elongated panel 11 with the second end of the slit lamp base 20 abutting the front recess 12.

The slit lamp base 20 is moveable upon the top side of the elongated panel 11 through the use of a slide apparatus. The slide apparatus is comprised of a cylindrical opening 22 near the second end of the slit lamp base 20 which cylindrical opening 22 extends from the first side to the second side of the slit lamp base 20. A horizontal cylindrical rod 24 is maintained within the cylindrical opening 22 with the horizontal cylindrical rod 24 extending parallel to the front recess 12 and terminating at the outward extensions 38. The ends of the horizontal cylindrical rod 24 are fixedly attached to a pair of brackets 26 which brackets 26 are fixedly attached to the top side of the elongated panel 11. The slit lamp microscope 18 is capable of being moved from side to side by sliding the slit lamp base 20 upon the horizontal cylindrical rod 24.

The eye examination or treatment requires the patient to place his or her chin in a chin support 14 and his or her forehead against a forehead support 16. The prior art structure containing the chin and forehead support 14, 16 would be fixedly attached to the table near the front edge where the patient is seated. To include a front recess 12 in the slit lamp table 10, it is necessary in the present invention to move the support structure for the chin and forehead supports 14, 16 away from the front edge of the elongated panel 11.

Figure 4:
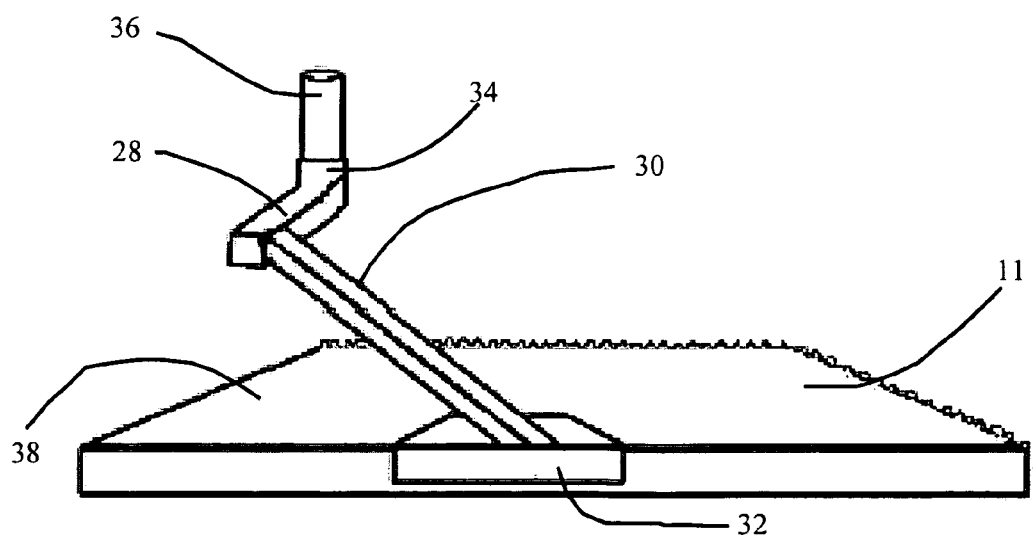
FIG. 4 is a side perspective view of the support apparatus for the chin and forehead support structure.

To properly support the chin and forehead supports 14, 16 away from the front edge of the elongated panel 11, the present invention includes a pair of horizontal tubing sections 28 which extend horizontally above and at right angles to the side edges and outward extensions 38 of the elongated panel 11. The horizontal tubing sections 28 terminate at the outside edges of the front recess 12. The horizontal tubing sections 28 have a top side, a bottom side, a first side, a second side, a first end and a second end. Referring to FIG. 4, fixedly attached to the first end of the horizontal tubing sections 28 is the top end of a section of angled square tubing 30. The bottom end of the angled square tubing 30 is fixedly attached to an L-shaped bracket 32. The L-shaped bracket 32 is fixedly attached to the longitudinal side edges of the elongated panel 11.

Fixedly attached to the second ends of the horizontal tubing sections 28 are a pair of vertical tubing sections 34 having a first open end a second open end. Fixedly attached to the first open end of the vertical tubing sections 34 are a pair of vertically extending cylindrical rods 36. The sides of the chin support 14 and forehead support 16 are movably attached to the vertically extending cylindrical rods 36, thereby allowing the chin and forehead supports 14, 16 to be adjusted about the cylindrical rods 36 to properly accommodate the individual being examined.

Contained on the bottom side of the elongated panel 11 is the pivoting arm (not shown) of the table support and near the longitudinal side edge of the elongated panel 11 is an electronics box 40 in which the electronic components (not shown) of the slit lamp microscope 18 are contained.

Various changes and departures may be made to the invention without departing from the spirit and scope thereof. Thus it is not intended that the invention be limited to what is described in the specification and illustrated in the drawings, rather only as set forth in the claims.

What is claimed is:

1. A slit lamp table for a handicapped person confined to a wheel chair or an overweight person comprising:
    a generally planar narrow elongated panel having a top side and a bottom side, two lateral end edges and two longitudinal side edges;
    a recess formed centrally in the lateral end edge of the elongated panel to accommodate the torso of a person occupying a wheel chair or an overweight person and to define at each side of the recess an outward extension;
    a support structure for chin and forehead supports which is fixedly attached to the longitudinal side edges of the elongated panel;
    a means for moving a slit lamp microscope about the elongated panel.

2. A slit lamp table as claimed in claim 1 in which the slit lamp table is in the form of an elongated panel with the space beneath the panel being substantially free of obstructions to facilitate the locating of a wheel chair in proper selected position with respect to the slit lamp table.

3. The device of claim 1, wherein a structure for maintaining the chin and forehead supports further comprises:
- a pair of horizontal tubing sections having a first end and a second end extending above and at right angles to the outward extensions of the slit lamp table;
- a pair of angled square tubing sections with the top end of the angled square tubing sections fixedly attached to the first ends of the horizontal tubing sections and the bottom end of the angled square tubing sections fixedly attached to an L-shaped bracket which L-shaped bracket is fixedly attached to the longitudinal side edges of the elongated panel;
- a pair of vertical tubing sections fixedly attached to the second ends of the horizontal tubing sections and a pair of vertically extending cylindrical rods fixedly attached to the vertical tubing sections;
- a chin support which is movably maintained between the vertically extending cylindrical rods; and
- a forehead support which is movably maintained between the vertically extending cylindrical rods.

4. The device of claim 1, wherein the means for moving a slit lamp microscope about the elongated panel is comprised of:
- a triangular shaped base having a first end, a second end, a first side and a second side upon which a slit lamp microscope is removably attached;
- a cylindrical opening adjacent to the second end of the base which cylindrical opening extends from the first side to the second side of the base;
- a horizontal cylindrical rod maintained within the cylindrical opening of the base with the horizontal cylindrical rod extending parallel to a front recess in the elongated panel and terminating at the outward extensions of the elongated panel;
- a pair of brackets which are fixedly attached to the top side of the elongated panel into which the ends of the horizontal cylindrical rod are maintained.

5. A slit lamp table comprising:
- a generally planar narrow elongated panel having a top side and a bottom side, two lateral end edges and two longitudinal side edges;
- a recess formed centrally in the lateral end edge of the slit lamp table with outward extensions defined at each side of the recess;
- a support structure for chin and forehead supports comprising:
  - a pair of horizontal tubing sections having a first end and a second end extending above and at a right angles to the outward extensions;
  - a pair of angled square tubing sections with the top end of the angled square tubing sections fixedly attached to the first ends of the horizontal tubing sections and the bottom end of the angled square tubing sections fixedly attached to an L-shaped bracket which L-shaped bracket is fixedly attached to the longitudinal side edges of the elongated panel;
  - a pair of vertical tubing sections fixedly attached to the second ends of the horizontal tubing sections and fixedly attached to the cylindrical tubing sections are a pair of vertically extending cylindrical rods;
  - a chin support which is movably maintained between the vertically extending cylindrical rods; and
  - a forehead support which is movably maintained between the vertically extending cylindrical rods;
- a means for moving a slit lamp microscope about the elongated panel is comprised of:
  - a triangular shaped base having a first end, a second end, a first side and a second side upon which a slit lamp microscope is removably attached;
  - a cylindrical opening adjacent to the second end of the base which cylindrical opening extends from the first side to the second side of the base;
  - a horizontal cylindrical rod maintained within the cylindrical opening of the base with the horizontal cylindrical rod extending parallel to a front recess in the elongated panel and terminating at the outward extensions of the elongated panel;
  - a pair of brackets which are fixedly attached to the top side of the elongated panel into which the ends of the horizontal cylindrical rod are fixedly attached.

* * * * *